United States Patent [19]

Cullo

[11] Patent Number: 5,091,579
[45] Date of Patent: Feb. 25, 1992

[54] ANILINE CATALYST

[75] Inventor: Leonard A. Cullo, Hempfield Township, Westmoreland County, Pa.

[73] Assignee: Aristech Chemical Corporation, Pittsburgh, Pa.

[21] Appl. No.: 379,854

[22] Filed: Jul. 14, 1989

[51] Int. Cl.⁵ .................... C07C 209/18; B01J 27/125
[52] U.S. Cl. .................................... 564/402; 502/231
[58] Field of Search .................. 502/231; 564/402

[56] References Cited

U.S. PATENT DOCUMENTS

| | | | |
|---|---|---|---|
| 2,471,647 | 5/1949 | Oblad et al. | 502/231 |
| 2,830,106 | 4/1958 | Good et al. | 502/231 |
| 2,968,676 | 1/1961 | Potter, Jr. et al. | 260/576 |
| 3,079,439 | 2/1963 | Potter, Jr. | 260/576 |
| 3,118,944 | 1/1964 | Addis | 260/576 |
| 3,272,865 | 9/1966 | Barker | 260/581 |
| 3,860,650 | 1/1975 | Becker et al. | 260/570 D |
| 3,944,613 | 3/1976 | Naramoto et al. | 260/576 |
| 4,400,537 | 8/1983 | Weil | 564/402 |

FOREIGN PATENT DOCUMENTS

| | | | |
|---|---|---|---|
| 127396 | 12/1984 | European Pat. Off. | 564/402 |
| 127396 | 12/1984 | European Pat. Off. | |
| 293483 | 12/1988 | European Pat. Off. | |
| 101317 | 9/1978 | Japan | 564/402 |

Primary Examiner—Carl F. Dees
Attorney, Agent, or Firm—William L. Krayer

[57] ABSTRACT

Amination of phenolic compounds by ammonia is accomplished in the presence of a gamma alumina containing a small amount of fluoride.

3 Claims, No Drawings

ANILINE CATALYST

TECHNICAL FIELD

This invention relates to a process for the production of aniline, and particularly to the production of aniline in high yields by the vapor phase reaction of phenol with ammonia in the presence of a fluorided low alkali containing alumina catalyst.

Additionally, the present invention relates to processes for preparing fluorided alumina catalysts for use in the production of aniline by the amination of phenol with ammonia.

BACKGROUND OF THE INVENTION

Aniline is an important industrial chemical widely used as an intermediate in the preparation of dyes, photographic chemicals, agricultural chemicals, di-isocynates and rubber vulcanization accelerators.

A major commercial process for the preparation of aniline is based upon the reduction of nitrobenzene with hydrogen. This process involves the need to utilize large quantities of nitric acid as a nitrating agent and comparably large quantities of alkali to neutralize the waste acid purge, which generates significant environmental problems. Large amounts of wastewater containing high concentrations of salts are produced and must be carefully discarded. Moreover, the process of nitration of benzene is considered a highly hazardous operation.

For the reasons cited above, the manufacture of aniline by reaction of phenol with ammonia has become of major interest.

A number of processes for producing aniline by reaction of phenol with ammonia have been disclosed utilizing silica alumina catalysts, as well as zirconia-alumina, titania-alumina, zirconia-silica phosphate and tungsten oxide (See Japanese Patent Publication No. 23571/1967, for example).

U.S. Pat. No. 3,860,650 teaches the use of a precipitated alumina gel containing silica leached with boric acid or hydrochloric acid to reduce sodium below 1 percent by weight. Comparative examples of alumina containing silica made from natural clays which were leached with boric acid or hydrochloric acid to reduce sodium below 1 wt percent were shown not to be effective An additional example using an alumina containing only traces of sodium was tested. The alumina was Catapal, obtained now from the Vista Chemical Corporation, but originally Continental Oil Company. The alumina is prepared by precipitation as a fine crystalline powder from solution in organic alcohol. The initial activity of this catalyst expressed as a relative rate constant (k) was 0.2 compared to the Example 1 and Example 2 catalysts of choice which had rate constants (k) of 1.0 and 1.6, respectively. A fresh quantity of Catapal was leached with hydrochloric acid and retested Its initial activity expressed as a relative rate constant (k) was 0.2.

In U.S. Pat. No. 3,272,865, processes are described for the production of aniline by reaction of phenol with ammonia using catalysts selected from a group consisting of silica-alumina having from 10 percent to 20 percent silica, silica-alumina having 10 percent to 20 percent alumina, zirconia-alumina, titania-alumina, phosphoric acid and tungsten oxide. These catalysts although producing effluents from the reactor containing from 80 wt percent to 88 wt percent aniline, suffer from rapid activity declines arising from the formation of carbonaceous coatings. Interruption of the process in order to regenerate the catalyst and restore activity is required after less than 100 hours of operation.

The '865 patent also recites an example of a commercial alumina sample substituted for the silica-alumina of Example 1 and under the same process conditions. As shown in the '865 patent Example 3, with the alumina catalyst the reaction proceeds very slowly as is evidenced by the low formation of aniline. At a temperature of 475° C., 45 percent of the phenol is converted to aniline. The inventor states that, "This example clearly shows that a gamma-alumina catalyst gives inferior conversions to phenol as compared to the catalysts of the instant invention."

In European Pat. No. Application No. 87907534.9 are disclosed processes for preparing aniline from a vapor phase reaction of phenol and ammonia, and for preparing the catalyst. As shown in Examples 2, 3, and 4, the preferred catalyst is a silica-alumina catalyst containing 9.9 wt percent silica having an alkali metal oxide content of less than 0.5 wt percent, said catalyst calcined at a temperature of 600° C. -900° C. followed by an acid treatment. The catalysts of European Application No. 87907534.9 show no loss in activity after 1000 hours of operation. This is compared to the silica-alumina catalysts, of low alkali content after acid treatment described in U.S. Pat. No. 3,860,650 which require regeneration after approximately 600 hours on stream.

Prior art which has addressed the desirability of developing a vapor phase process for production of aniline by reaction of phenol with ammonia have tended to focus on the use of silica-alumina catalysts. Such catalysts have in varying degrees been deficient in stability, may require regeneration after 40–600 hours or activity, and typically require elevated temperatures of 375° C. for 98–99 percent conversion of phenol.

OBJECT OF THE INVENTION

It is the object of the present invention to solve the above-mentioned problems encountered in the prior art, and provide a process for preparing aniline by reacting phenol with ammonia whereby, through the use of a catalyst of this invention, extended cycle times (several years), high phenol conversions and high aniline selectivity are achieved at reaction temperatures lower than those employed in prior art processes.

SUMMARY OF THE INVENTION

The process of preparing aniline which comprises reacting phenol with ammonia is characterized by the presence of a fluorided alumina catalyst, preferably of an alkali content of less than 1.0 wt% and a surface area in excess of 150 m$^2$/g. The catalyst is made by treating a pseudoboehmite alumina with a fluoride compound either prior to or after calcination to a gamma form of alumina.

DETAILED DESCRIPTION OF THE INVENTION

The catalytic amination of phenol with ammonia is well-known. The process can be extended to the amination of other phenolic compounds utilizing the catalyst of this invention. Typical phenolic compounds which may be aminated with my catalyst using ammonia include phenol, naphthol, dihydroxybenzenes, and hydroquinones.

The molar ratio of ammonia to hydroxy compound in my process suitably ranges from 2/1 to 100/1. Preferably the range is about 5/1 to 30/1. Initial reaction temperatures range from 250° C. to 500° C. depending upon the particular compound to be aminated. For phenol, 250° C. to 500° C. is a useful range, but the preferred initial reaction temperature ranges from 320°–400° C. As the catalyst ages, reactor temperatures should be incrementally increased within the discretion of the operator in order to maintain the desired degree of hydroxy conversion.

Although the catalysts of this invention are stable to over 600° C. reactor temperature, it is preferable to interrupt operations when reactor temperatures reach 425° C. The catalyst loses activity very gradually during operation as a result of accumulating carbonaceous material This carbonaceous deposit can be readily removed by passing an oxygen containing gas over the catalyst at a temperature sufficient to oxidize the carbonaceous deposit Regeneration temperatures ranging from 450° C. to 600° C. are most preferred. The combustion is controlled within these limits in order to minimize damage to the catalyst surface as well as to minimize potential adverse effects upon the reactor metallurgy.

The rate of burning and thus the regeneration temperature may be controlled by adjustment of the inlet temperature of the regeneration gas as well as its quantity and by adjustment of the oxygen content of the regeneration gas.

The alumina catalysts of this invention which respond most favorably to the fluoriding treatment are based on materials designated pseudo boehmites. These aluminas, such as the Catapal products of Vista Chemical, are generally produced by precipitation of aluminum salts or by hydrolysis of aluminum alcoholates. By virtue of their manufacturing processes virtually all of the alkali metals are removed and the pseudo boehmite aluminas of commerce tend to contain less than 0.1 wt% alkali metals. Calcination will convert the alumina from the pseudoboehmite form to gamma alumina. Although I do not intend to be bound by the concept, it is believed that the presence of significant alkali content will depress total acidity of the catalyst, and tend to neutralize weak acid sites as well as intermediate and strong acid sites. My catalysts are made by treating a pseudoboehmite alumina with a fluoride compound either prior to or after calcination to a gamma form of alumina. Calcination should be conducted at about 400°–550° C. for at least 4 hours, preferably about 5 hours.

The process of fluoriding an alumina containing low levels of alkali metal appears to increase total alumina acidity, as measured by ammonia desorption, by up to 50%. Many other anions are known to perform the function of increased acidity when impregnated on alumina. However, fluoride anions appear more selectively to increase the weaker acid sites on alumina. Weaker acid sites on alumina are defined as those sites which desorb ammonia at temperatures below about 300° C.

Aluminas other than pseudo boehmites, such as activated aluminas will also respond well to fluoride impregnation particularly when the alkali metal content on such aluminas is reduced below 1 wt% and preferably below 0.1 wt%. Although the presence of fluoride in concentration as low as 0.2% may have a noticeable beneficial effect in my invention, I prefer for my final product to contain at least about 0.5% fluoride.

Although again I do not intend to be bound by the concept, it is believed that the amination of phenols with ammonia is catalyzed by weak acid sites. These weak acid sites accelerate the amination reactions but only in a minor way contribute to cracking and polymerization reactions. It is these cracking and polymerization reactions which deposit carbonaceous material on the catalyst surfaces leading to a rapid decline in catalyst activity. Strong acid catalysts such as mordenite, dealuminated Y zeolite, and silica alumina cracking catalysts have demonstrated excellent initial amination activities. However, accompanying the amination reactions are extensive cracking and polymerization reactions and these initially highly active catalysts rapidly decline in activity.

Standard Test Conditions

Performance tests conducted to evaluate and rank various catalysts were carried out in a 1" I.D. reactor with a catalyst charge of approximately 100 ml. Three or four phenol conversions over a range of liquid hourly space velocities (LHSV) were measured for each example and a plot of conversion versus 1/LHSV was drawn in order to calculate the slope of the curve at 50% conversion which is referred to as the zero order rate constant (k). The value of the slope is normalized by dividing that value by the reactor contact time in seconds. High values of k indicate relatively greater activity of the catalyst under test. Virtually all of the catalysts tested demonstrated selectivities to aniline greater than 99.5 wt% under standard test conditions described immediately below. Catalysts were compared by varying LHSV and determining the k while other reactor parameters were held constant:

| | |
|---|---|
| Ammonia/Phenol (molar ratio) | 20 |
| Average Reactor Temperature °C. | 356 |
| Reactor Pressure psia | 240 |

$$\text{Conversion (\%)} = \frac{\text{Number of moles of phenol reacted}}{\text{Number of moles phenol fed}} \times 100$$

$$\text{Selectivity (\%)} = \frac{\text{Number of moles aniline formed}}{\text{Number of moles phenol reacted}} \times 100$$

Selectivities are reported below at the highest conversion rate obtained for the catalyst tested. In each case lower conversion rates yielded higher selectivities, as persons skilled in the art would expect.

EXAMPLE 1

Catalpal B alumina powder, characterized as a pseudo boehmite alumina, is produced by Vista Chemical Company. This alumina is prepared by the hydrolysis of aluminum alcholates. The powder was mix-mulled with water and extruded through a die. The wet extrusions were dried at 210° C. for 3 hours and calcined at 500° C. for five hours, to produce a gamma alumina.

Analysis of the extruded gamma alumina catalyst was as follows:

| Component | Weight Percent |
|---|---|
| Alumina ($Al_2O_3$) | 99 |
| Sodium ($Na_2O$) | <0.1 |
| Iron ($Fe_3O_4$) | <0.1 |
| Water | balance |
| Surface Area $m^2/g$ | 193 |
| Pore Volume cc/g | 0.6 |
| Packed Density g/cc | 0.68 |

After 72 hours of testing and varying the LHSV from about 0.1 to 0.02, a rate constant k of 38.8 was calculated and a selectivity to aniline of 99.8% was obtained at the highest conversion rate.

EXAMPLE 2

The extrusions of Example 1 were treated with an ammonium fluoride solution using a pore saturation technique. 100 grams of extrusions contained a total pore volume of 60 cc. An ammonium fluoride solution containing 3.9 grams of $NH_4F$ in 60 cc of water was slowly sprayed onto the extrusions while mixing the extrusions to assure uniform dispersion of the solution. Upon completion of solution addition, the extrusions appeared slightly damp. The impregnated extrusions were dried at 210° C. for 3 hours. After drying, the impregnated extrusions were calcined at 500° C. for 5 hours. Analysis of the calcined extrusions showed a fluoride content of 2 wt%.

The fluorided Catapal extrusions were charged to the reactor and tested under standard test conditions. A rate constant (k) of 81 was calculated and a selectivity to aniline of 99.8% was obtained at the highest conversion rate.

Example 3

An alumina powder mixture consisting of 65% Catapal B (pseudo boehmite alumina) and 35% of a Versal pseudo boehmite alumina, which is produced by LaRoche Chemicals was extruded and calcined 5 hours at 500° C. to convert them to gamma alumina having a pore volume of 0.65 w/g. The extrusions were impregnated with a 5.6% by weight ammonium fluoride solution following the procedure of Example 2. After drying and calcining the impregnated extrusions, the fluoride content was determined to be 1.9 wt%. The fluorided extrusions were charged to a reactor and tested under standard reactor conditions. A rate constant (k) of 120 was calculated with an aniline selectivity of 99.8 wt% at the highest conversion rate. After 100 hours of test, no change in rate constant was detected.

EXAMPLE 4

The Catapal B alumina powder received from Vista Chemicals was impregnated in powder form by a pore saturation technique using an aqueous solution of ammonium fluoride sufficient to add 2 wt% fluoride after complete adsorption of the liquid into the alumina pores. The powder was extruded following Example 1 and after calcination at 550° C. for 5 hours was charged to the reactor and tested under standard reactor conditions of Example 1. A reaction rate constant (k) of 87.2 was calculated with an aniline selectivity of 99.7% at the highest conversion rate.

EXAMPLE 5

The unimpregnated extrusions of Example 3 were used to determine the activity of fluorided alumina containing lower levels of fluoride. The impregnation solution used in Example 3 for extrusions with a pore volume of 0.65 cc/g was 5.6 wt% aqueous solution of ammonium fluoride. For preparation of catalysts of this Example 5, the solution was diluted to 1.96 wt% ammonium fluoride. After drying and calcining at 500° C. for 5 hours, the residual fluoride on the gamma alumina catalyst measured 0.67 wt% F. Example 6

Alumina powder, Versal 850, received from LaRoche Industries was extruded and calcined as in Example 1.

The powder had the following characteristics as received.

| Component | Weight Percent |
| --- | --- |
| Alumina ($Al_2O_3$) | 97 |
| Sodium ($Na_2O$) | 0.02 |
| Iron ($Fe_2O_3$) | 0.03 |
| Silica ($SiO_2$) | 0.06 |
| $SO_4$ | 0.02 |
| Cl | 0.07 |
| Formate | 2 |
| Water | balance |

The Versal 850 powder was extruded as in Example 1 and the extrusions calcined for 5 hours at 500° C. The extrusions were impregnated by a pore saturation procedure as in Example 2 with sufficient aqueous ammonium fluoride solution to deposit 2 wt% fluoride. The fluorided alumina extrudates after drying were calcined at 550° C. for 5 hours and tested in the standard reactor test. A rate constant (k) of 88.1 was calculated with an aniline selectivity of 99.8% at the highest conversion rate.

The test run was extended to determine catalyst activity decline rates. However, after 1000 hours of test, no activity decline could be detected and the test was concluded. Example 7

Para-cresol and ammonia were fed to the reactor in a 1/18 molar ratio and at the following test conditions: Reactor temperature 355° C; reactor pressure 190 psig; LHSV 0.094. Analysis of the product revealed that conversion of para-cresol was 99 wt% with a selectivity to para-toluidine of 95% obtained.

I claim:

1. Method of aminating a compound selected from phenols and substituted phenols comprising contacting said compound with ammonia in the vapor phase in the presence of a gamma alumina catalyst which contains about 0.5% to about 4% fluoride by weight and less than about 1 percent by weight alkali metal.

2. Method of claim 1 in which said compound is para-cresol.

3. Method of making aniline comprising reacting phenol and ammonia at a temperature from about 320° to about 400° C. in the presence of a catalyst derived by calcination from pseudoboehmite containing less than about 1% alkali metal, said catalyst containing about 0.5% to about 4% fluoride by weight.

* * * * *